(12) United States Patent
Namose

(10) Patent No.: US 7,057,175 B2
(45) Date of Patent: Jun. 6, 2006

(54) INFRARED ABSORPTION MEASUREMENT METHOD, INFRARED ABSORPTION MEASUREMENT DEVICE, AND METHOD OF MANUFACTURING SEMICONDUCTOR DEVICE

(75) Inventor: Isamu Namose, Suwa (JP)

(73) Assignee: Seiko Epson Corporation, Tokyo (JP)

( * ) Notice: Subject to any disclaimer, the term of this patent is extended or adjusted under 35 U.S.C. 154(b) by 143 days.

(21) Appl. No.: 10/756,413

(22) Filed: Jan. 14, 2004

(65) Prior Publication Data
US 2004/0200963 A1 Oct. 14, 2004

(30) Foreign Application Priority Data
Jan. 20, 2003 (JP) ............................. 2003-011115

(51) Int. Cl.
- *G01J 5/02* (2006.01)
- *G01N 9/00* (2006.01)
- *G01N 19/10* (2006.01)
- *G01N 21/00* (2006.01)
- *G01N 25/00* (2006.01)
- *G01N 27/00* (2006.01)
- *G01N 29/02* (2006.01)

(52) U.S. Cl. .................. 250/339.13; 356/437; 356/438; 356/439; 73/23.2

(58) Field of Classification Search ............ 250/339.12, 250/339.13, 339.09; 356/437, 438, 439
See application file for complete search history.

(56) References Cited

U.S. PATENT DOCUMENTS

| | | | | |
|---|---|---|---|---|
| 5,821,537 A | * | 10/1998 | Ishihara et al. | ........ 250/339.13 |
| 6,642,521 B1 | * | 11/2003 | Namose et al. | ........ 250/339.09 |
| 6,794,649 B1 | * | 9/2004 | Thrash et al. | .......... 250/339.13 |
| 2004/0188621 A1 | | 9/2004 | Namose | |

FOREIGN PATENT DOCUMENTS

| | | |
|---|---|---|
| JP | A 5-249040 | 9/1993 |
| JP | A 05-332921 | 12/1993 |
| JP | 6-281578 | 10/1994 |
| JP | A 09-178656 | 7/1997 |
| JP | A 10-221253 | 8/1998 |
| JP | A 11-258156 | 9/1999 |
| JP | A 2002-82049 | 3/2002 |
| JP | A 2002-082049 | 3/2002 |

* cited by examiner

*Primary Examiner*—David Porta
*Assistant Examiner*—Frederick F. Rosenberger
(74) *Attorney, Agent, or Firm*—Oliff & Berridge, PLC

(57) ABSTRACT

An infrared absorption measurement method includes: (a) measuring infrared absorption of a measurement target component in a state in which a sample gas including the measurement target component is decompressed; (b) calculating an absorption area in a peak region of the measurement target component in the infrared absorption shown in a graph which shows the relationship between the wave number and absorbance of the sample gas; and (c) calculating a concentration of the measurement target component in the sample gas based on the absorption area and pressure of the sample gas during decompression.

11 Claims, 10 Drawing Sheets

$CF_4$

INFRARED ABSORPTION MEASUREMENT METHOD, INFRARED ABSORPTION MEASUREMENT DEVICE, AND METHOD OF MANUFACTURING SEMICONDUCTOR DEVICE

Japanese Patent Application No. 2003-11115 filed on Jan. 20, 2003, is hereby incorporated by reference in its entirety.

BACKGROUND OF THE INVENTION

The present invention relates to an inexpensive and highly accurate infrared absorption measurement method and an infrared absorption measurement device.

The present invention also relates to a method of manufacturing a semiconductor device using the infrared absorption measurement method.

In the case of measuring the infrared absorption of a sample (see Japanese Patent Application Laid-open No. 2002-82049, for example), a cell having a suitable cell length is appropriately selected depending on the concentration of the sample. If the concentration of the sample is too high, a cell having a greater cell length must be used since the absorbance is saturated. Specifically, a plurality of cells must be provided corresponding to the concentration of the sample. However, since the cell used for infrared absorption measurement is expensive, the measurement cost is increased by providing a plurality of cells.

BRIEF SUMMARY OF THE INVENTION

The present invention may provide an inexpensive and highly accurate infrared absorption measurement method and an infrared absorption measurement device.

The present invention may further provide a method of manufacturing a semiconductor device using the infrared absorption measurement method.

An infrared absorption measurement method according to one aspect of the present invention includes:

(a) measuring infrared absorption of a measurement target component in a state in which a sample gas including the measurement target component is decompressed;

(b) calculating an absorption area in a peak region of the measurement target component in the infrared absorption shown in a graph which shows the relationship between the wave number and absorbance of the sample gas; and (c) calculating a concentration of the measurement target component in the sample gas based on the absorption area and pressure of the sample gas during decompression.

A method of manufacturing a semiconductor device according to another aspect of the present invention, includes calculating a concentration of a measurement target component in a sample gas by using the above infrared absorption measurement method, wherein the measurement target component is included in a gas discharged from semiconductor manufacturing equipment.

A first infrared absorption measurement device according to a further aspect of the present invention includes:

a pump which decompresses a sample gas including a measurement target component; and an infrared absorption analysis device which measures infrared absorption of the measurement target component in the sample gas decompressed by the pump.

A second infrared absorption measurement device according to a still further aspect of the present invention includes:

an infrared absorption analysis device which includes first and second cells for measuring infrared absorption and measures infrared absorption of a measurement target component in a sample gas;

a first line for introducing the sample gas into the first cell; and a second line for introducing the sample gas into the second cell, wherein pressure of the sample gas in the first cell differs from pressure of the sample gas in the second cell.

A third infrared absorption measurement device according to a yet further aspect of the present invention includes:

an infrared absorption analysis device which includes a cell for measuring infrared absorption and measures infrared absorption of a measurement target component in a sample gas;

a sample gas inlet switch section; and first and second lines which are connected in parallel with the sample gas inlet switch section and introduce the sample gas into the cell, wherein the sample gas inlet switch section has a function of introducing the sample gas into one of the first line and the second line, wherein the sample gas is introduced into the cell from one of the first line and the second line, and wherein pressure of the sample gas introduced into the cell from the first line differs from pressure of the sample gas introduced into the cell from the second line.

DETAILED DESCRIPTION OF THE EMBODIMENT

Figure 1:
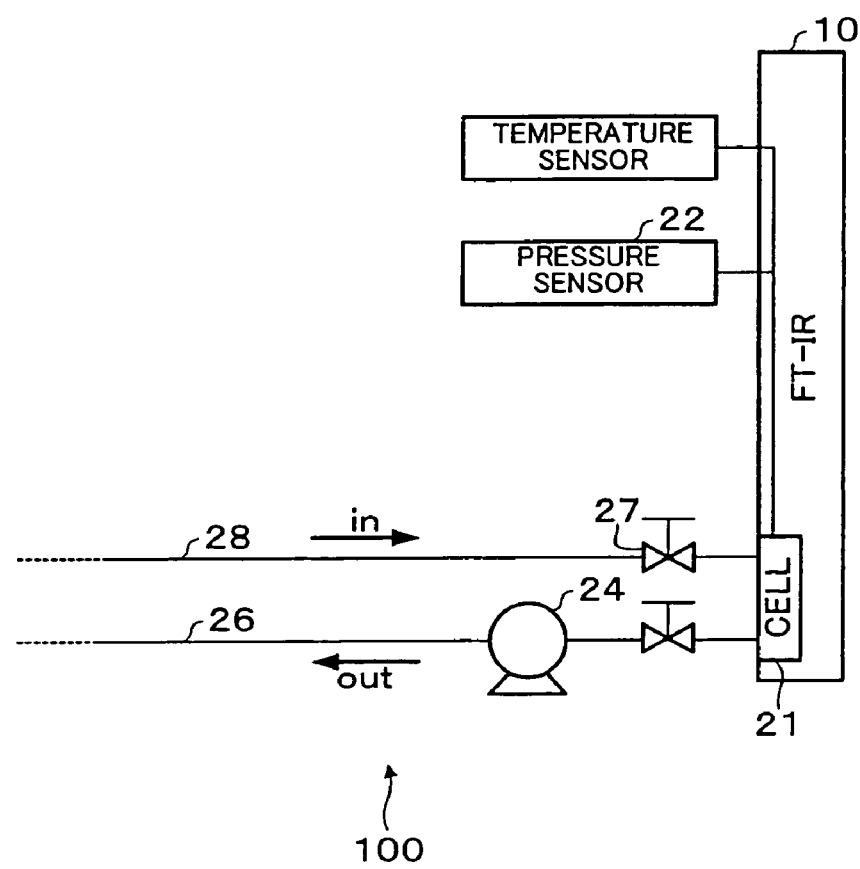
FIG. 1 schematically shows an infrared absorption measurement device in a first embodiment.

An infrared absorption measurement method according to one embodiment of the present invention includes:

(a) measuring infrared absorption of a measurement target component in a state in which a sample gas including the measurement target component is decompressed;

(b) calculating an absorption area in a peak region of the measurement target component in the infrared absorption shown in a graph which shows the relationship between the wave number and absorbance of the sample gas; and (c) calculating a concentration of the measurement target component in the sample gas based on the absorption area and pressure of the sample gas during decompression.

According to this infrared absorption measurement method, since the infrared absorption can be measured while decompressing the sample gas according to the concentration of the measurement target component, it is unnecessary to replace a cell used for infrared absorption measurement according to the concentration of the measurement target component. This enables cost necessary for measurement to be reduced. As a result, infrared absorption can be measured at low cost with high accuracy.

Moreover, the period of time necessary for the sample gas to be introduced into the cell and discharged from the cell can be shorter than the case of measuring the sample gas under normal pressure by measuring the infrared absorption while introducing the sample gas in a decompressed state. Therefore, the period of time necessary for the measurement can be reduced, whereby the measurement can be efficiently performed. The "normal pressure" used herein refers to atmospheric pressure.

The infrared absorption measurement method of the present invention may have the following features.

A temporary concentration $M_1$ corresponding to the absorption area may be calculated in the step (c) by referring to a calibration curve which represents the relationship between the concentration and absorption area of a reference gas including the target component, and when pressure of the reference gas including the measurement target component used to create the calibration curve during infrared absorption measurement is $P_1$ and the pressure of the sample gas during the decompression is $P_2$, a concentration $M_2$ of the sample gas may be expressed by the following equation.

$$M_2 = M_1 P_1 / P_2$$

The calibration curve shows the relationship between the absorption area of the measurement target component and the concentration of the measurement target component of the reference gas corresponding to the absorption area under predetermined pressure.

According to this method, the temporary concentration $M_1$ (see equation (1)) can be set within the concentration range which allows the concentration $M_2$ of the measurement target component to be accurately obtained by adjusting the pressure $P_2$ of the sample gas during decompression. This enables the concentration $M_2$ of the measurement target component to be accurately measured based on the equation (1) with reference to the calibration curve.

An infrared absorption region of the measurement target component shown in the graph may include a main peak region and a sub-peak region in an infrared absorption region, and the peak region may be the main peak region.

According to this method, even if the concentration of the measurement target component is extremely high, the concentration of the measurement target component can be accurately measured without replacing the cell by decompressing the sample gas.

This infrared absorption measurement method may further includes:

(d) measuring the infrared absorption of the measurement target component in the sample gas under pressure differing from the pressure of the sample gas in the step (a);

(e) calculating the absorption area based on the peak region of the measurement target component in the infrared absorption measured in the step (d);

(f) calculating the concentration of the measurement target component in the sample gas based on the absorption area calculated in the step (e) and the pressure of the sample gas in the step (d); and (g) comparing the concentration of the measurement target component calculated in the step (c) with the concentration of the measurement target component calculated in the step (f).

According to this method, the infrared absorption can be measured with higher accuracy by comparing the concentrations of the measurement target components obtained from the infrared absorption measured by using each of the cells.

The pressure of the sample gas in the step (d) may be normal pressure.

The measurement target component may be included in a gas discharged from semiconductor manufacturing equipment.

A method of manufacturing a semiconductor device according to another embodiment of the present invention includes:

calculating a concentration of a measurement target component in a sample gas by using the above infrared absorption measurement method, wherein the measurement target component is included in a gas discharged from semiconductor manufacturing equipment.

According to this method of manufacturing a semiconductor device, since the infrared absorption is measured in the cell in a state in which the sample gas is decompressed, the period of time in which the sample gas resides in the cell can be shorter than the case of measuring the sample gas under normal pressure. This prevents solid products included in the sample gas and discharged from the semiconductor manufacturing equipment together with the discharged gas from adhering to the cell.

A first infrared absorption measurement device according to a further aspect of the present invention includes:

a pump which decompresses a sample gas including a measurement target component; and an infrared absorption analysis device which measures infrared absorption of the measurement target component in the sample gas decompressed by the pump.

According to the first infrared absorption measurement device, the same effect as the above infrared absorption measurement method can be obtained.

A second infrared absorption measurement device according to a still further aspect of the present invention includes:

an infrared absorption analysis device which includes first and second cells for measuring infrared absorption and measures infrared absorption of a measurement target component in a sample gas;

a first line for introducing the sample gas into the first cell; and a second line for introducing the sample gas into the second cell, wherein pressure of the sample gas in the first cell differs from pressure of the sample gas in the second cell.

According to the second infrared absorption measurement device, the concentration of the measurement target component which is measured more accurately can be used as the measurement result.

In this case, the infrared absorption of the measurement target component in the sample gas in the first cell and the infrared absorption of the measurement target component in the sample gas in the second cell may be measured at the same time.

Therefore, the measurement target components included in the sample gases in the first and second cells can be measured at the same time in a state in which the sample gas in the first cell and the sample gas in the second cell are set under different pressures, and the concentrations of the measurement target components obtained from the infrared absorption measured by using each of the cells can be compared. This enables infrared absorption to be measured with higher accuracy.

A third infrared absorption measurement device according to a yet further embodiment of the present invention includes:

an infrared absorption analysis device which includes a cell for measuring infrared absorption and measures infrared absorption of a measurement target component in a sample gas;

a sample gas inlet switch section; and first and second lines which are connected in parallel with the sample gas inlet switch section and introduce the sample gas into the cell, wherein the sample gas inlet switch section has a function of introducing the sample gas into one of the first line and the second line, wherein the sample gas is introduced into the cell from one of the first line and the second line, and wherein pressure of the sample gas introduced into the cell from the first line differs from pressure of the sample gas introduced into the cell from the second line.

According to the third infrared absorption measurement device, since the pressure of the sample gas introduced from the first line differs from the pressure of the sample gas introduced from the second line, the sample gas can be measured under a more suitable pressure corresponding to the concentration of the measurement target component. This enables the concentration of the measurement target component to be measured more accurately.

Moreover, infrared absorption can be measured by introducing the decompressed sample gas through the first line when the concentration of the measurement target component is high, and introducing the sample gas under normal pressure through the second line when the concentration of the measurement target component is low, by switching the three-way valve. This makes it unnecessary to replace the cell according to the concentration of the measurement target component included in the sample gas. Therefore, cost can be reduced.

In this case, the sample gas inlet switch section may be a three-way valve, and the sample gas may be introduced into the cell from one of the first line and the second line by switching the three-way valve.

Embodiments of the present invention are described below with reference to the drawings.

1. First Embodiment 1-1. Infrared Absorption Measurement Device

FIG. 1 schematically shows an infrared absorption measurement device 100 in the present embodiment.

In the infrared absorption measurement device 100 in the present embodiment, a sample gas including a measurement target component is introduced into an infrared absorption analysis device 10 through a gas inlet line 28, and infrared absorption of the measurement target component is measured by using the infrared absorption analysis device 10. Specifically, the measurement target component included in the sample gas is the target of infrared absorption measurement.

The sample gas includes at least one measurement target component. In the present embodiment, the case where the sample gas includes one measurement target component ($CHF_3$) is described as an example.

In the infrared absorption measurement device 100, a valve 27 is provided in the middle of the gas inlet line 28, as shown in FIG. 1. A needle valve may be used as the valve 27, for example. In the infrared absorption measurement device 100, a pump 24 is provided in the middle of a discharge line 26. The pressure of the sample gas can be controlled by using the valve 27 and the pump 24. In more detail, the valve 27 and the pump 24 are used to decompress the sample gas. In more detail, the sample gas introduced into the gas inlet line 28 is decompressed by using the valve 27 and the pump 24, and introduced into the infrared absorption analysis device 10. In the infrared absorption analysis device 10, infrared absorption is measured in a state in which the sample gas is decompressed.

After the measurement, the sample gas is discharged from the infrared absorption analysis device 10 through the discharge line 26.

FIG. 1 illustrates the case where a Fourier transform infrared spectrometer (FT-IR) is used as the infrared absorption analysis device 10. However, the type of the infrared absorption analysis device 10 is not limited. In the following description, measurement data is the experimental result obtained by using IGA2000 manufactured by MIDAC Corporation as the FT-IR. In the measurement, a cell having a length of 1 cm was used.

1-2. Infrared Absorption Measurement Method

An infrared absorption measurement method using the infrared absorption measurement device 100 shown in FIG. 1 is described below in detail.

1-2-1. Measurement of Infrared Absorption

In the infrared absorption measurement device 100, infrared absorption of the measurement target component ($CHF_3$) is measured by using the infrared absorption analysis device 10 in a state in which the sample gas including the measurement target component is decompressed. In more detail, the decompressed sample gas is introduced into a cell 21 in the infrared absorption analysis device 10, and infrared absorption of the measurement target component is measured by using the cell 21. The pressure $P_2$ of the sample gas in the cell 21 is detected by using a pressure sensor 22. After the measurement, the sample gas is discharged from the cell 21, and discharged to the outside through the discharge line 26.

1-2-2. Calculation of Absorption Area

The absorption area in the peak region of the measurement target component is calculated from the infrared absorption spectrum of the measurement target component obtained by using the infrared absorption analysis device 10. The absorption area may be calculated by using commercially available software.

1-2-3. Calculation of Concentration of Measurement Target Component

The concentration of the measurement target component is calculated from the absorption area obtained in the above description 1-2-2. and the pressure of the sample gas during decompression obtained in the above description 1-2-1.

In more detail, the temporary concentration $M_1$ corresponding to the absorption area is calculated by referring to a calibration curve which represents the relationship between the concentration and absorption area of a reference gas including the target component. The calibration curve shows the relationship between the concentration and the absorption area of the measurement target component, and is created by using the following method. A known calibration curve may be used instead of creating the calibration curve.

(I) Creation of Calibration Curve

The calibration curve is obtained by calculating the absorption area by measuring the infrared absorption of the gas including a known concentration of the measurement target component, calculating the absorption area while changing the concentration of the measurement target component, and plotting the absorption area versus the concentration. In the measurement of the concentration of the measurement target component for creating the calibration curve, the pressure of the gas is made constant. The pressure of the gas is referred to as $P_1$.

In the infrared absorption, the concentration of the measurement target component in the gas to be measured is proportional to the absorption area of the measurement target component under conditions where the pressure of the gas is constant. Therefore, the calibration curve is obtained by plotting the absorption area versus the concentration of the measurement target component under conditions where the pressure of the gas is constant.

Figure 6:
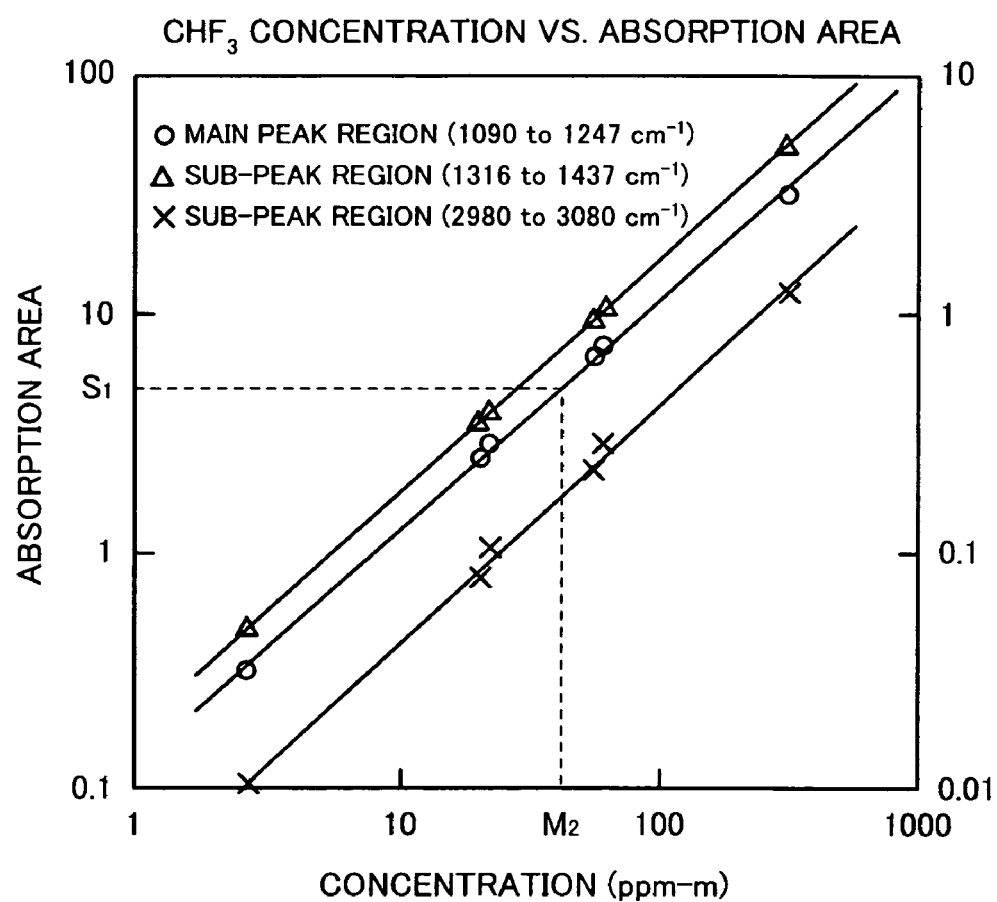
FIG. 6 shows the relationship (calibration curve) between concentration and absorption area of $CHF_3$ in a main peak region and a sub-peak region in another graph showing the relationship between the wave number and absorbance of $CHF_3$.

As an example, the case where the measurement target component is $CHF_3$ is described below. FIG. 6 shows the calibration curve based on $CHF_3$. This calibration curve shows the absorption area versus the concentration of the measurement target s component ($CHF_3$). In FIG. 6, the vertical axis indicates the absorption area, and the horizontal axis indicates the $CHF_3$ concentration.

$CHF_3$ has a main peak region (1090 to 1247 $cm^{-1}$) and two sub-peak regions (1316 to 1437 $cm^{-1}$ and 2980 to 3080 $cm^{-1}$) in the infrared absorption region. Therefore, in the case where the measurement target component is $CHF_3$, calibration curves can be created for each of the main peak region and the sub-peak regions. FIG. 6 shows the calibration curve based on the main peak region and two calibration curves based on two sub-peak regions.

The present embodiment illustrates the case where the $CHF_3$ concentration is calculated by calculating the absorption area based on the main peak region. In FIG. 6, the vertical axis (absorption area) of the calibration curve based on the main peak region is indicated by a value using the scale on the left of the graph, and the vertical axis of the calibration curve based on the sub-peak region is indicated by a value using the scale on the right. The calibration curve shown in FIG. 6 is based on measurement results obtained by measuring infrared absorption of the gas including the measurement target component ($CHF_3$) under normal pressure.

(II) Calculation of Concentration

As shown in FIG. 6, the resulting absorption area in the case where the measurement target component is $CHF_3$ is referred to as $S_1$, for example. In the calibration curve based on the main peak region shown in FIG. 6, the concentration (temporary concentration) of $CHF_3$ in the gas is $M_1$.

In the case where the pressure of the gas is constant, the absorption area of the measurement target component is proportional to the concentration of the measurement target component. In the case where the absorption area of the measurement target component is constant, the concentration of the measurement target component is inversely proportional to the pressure of the measurement target component.

If the pressure of the gas including the measurement target component used to create the calibration curve during infrared absorption measurement is $P_1$, and the pressure of the sample gas during decompression is $P_2$, the concentration $M_2$ of the measurement target component in the sample gas is expressed by the following equation (1).

$$M_2 = M_1 P_1 / P_2 \quad (1)$$

Therefore, the concentration $M_2$ of the measurement target component in the sample gas is obtained based on the equation (1) by measuring the temporary concentration $M_1$ and the pressures $P_1$ and $P_2$.

1-3. Effect

The effects in the present embodiment are described below. First, a conventional infrared absorption measurement method is described in order to compare its effects with the effects in the present embodiment.

1-3-1. Conventional Infrared Absorption Measurement Method

In a conventional infrared absorption measurement, a cell having a suitable cell length must be selected corresponding to the concentration of the measurement target component in the gas to be measured. Generally, a cell having a small cell length is used when the concentration of the measurement target component is high, and a cell having a large cell length is used when the concentration of the measurement target component is low.

Figure 7:
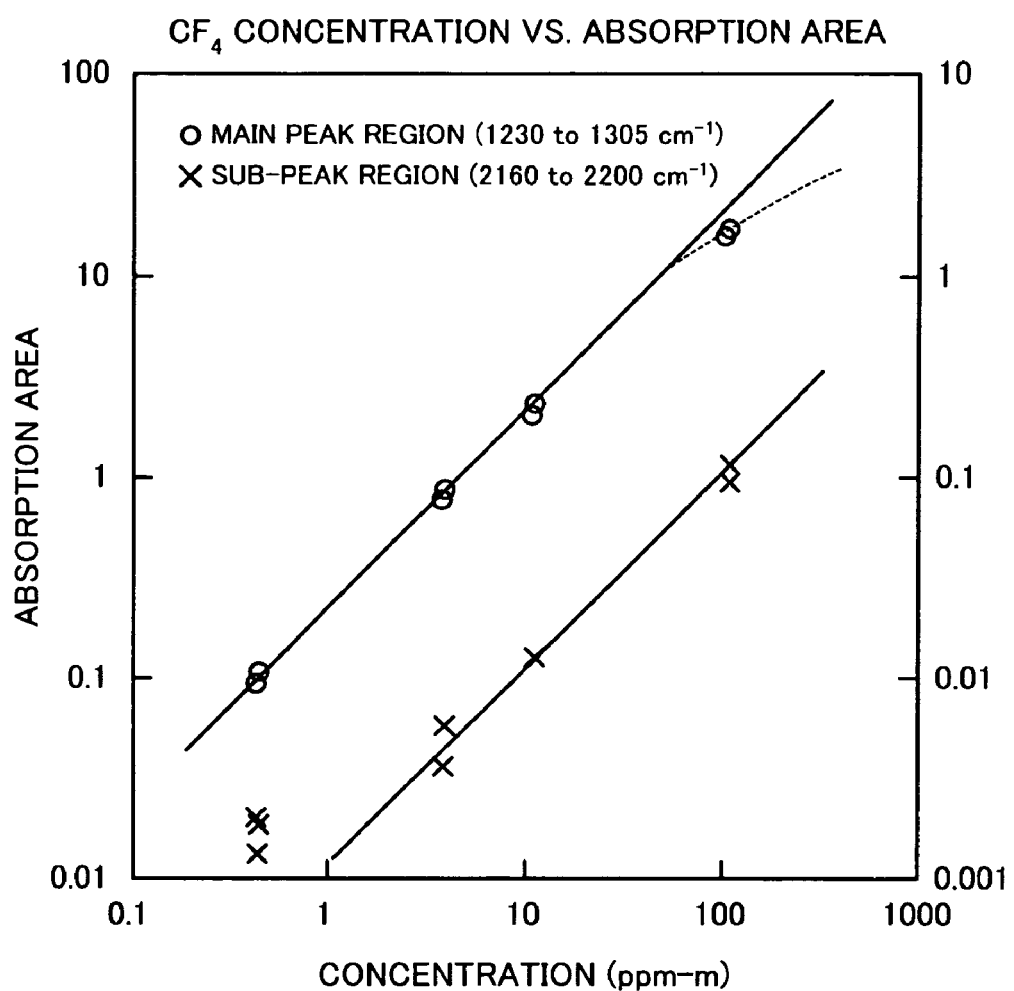
FIG. 7 shows the relationship (calibration curve) between concentration and absorption area of $CF_4$ in a main peak region and a sub-peak region in another graph showing the relationship between the wave number and absorbance of $CF_4$.

There may be a case where an accurate calibration curve cannot be obtained depending on the type or concentration of the measurement target component. As an example, the case where the measurement target component is $CF_4$ is described below. FIG. 7 shows the calibration curve based on $CF_4$. In FIG. 7, the vertical axis (absorption area) of the calibration curve based on the main peak region is indicated by a value using the scale on the left of the graph, and the vertical axis of the calibration curve based on the sub-peak region is indicated by a value using the scale on the right. The calibration curve shown in FIG. 7 is based on the measurement results obtained by measuring infrared absorption in a state in which the pressure of the gas including the measurement target component ($CF_4$) is approximately equal to atmospheric pressure.

As shown in FIG. 7, in the case of using $CF_4$ as the measurement target component, linearity of the calibration curve based on the main peak region is lost in the region in which the concentration of the measurement target component is high (see dotted line in FIG. 7). The reasons therefor are described below.

Figure 8:
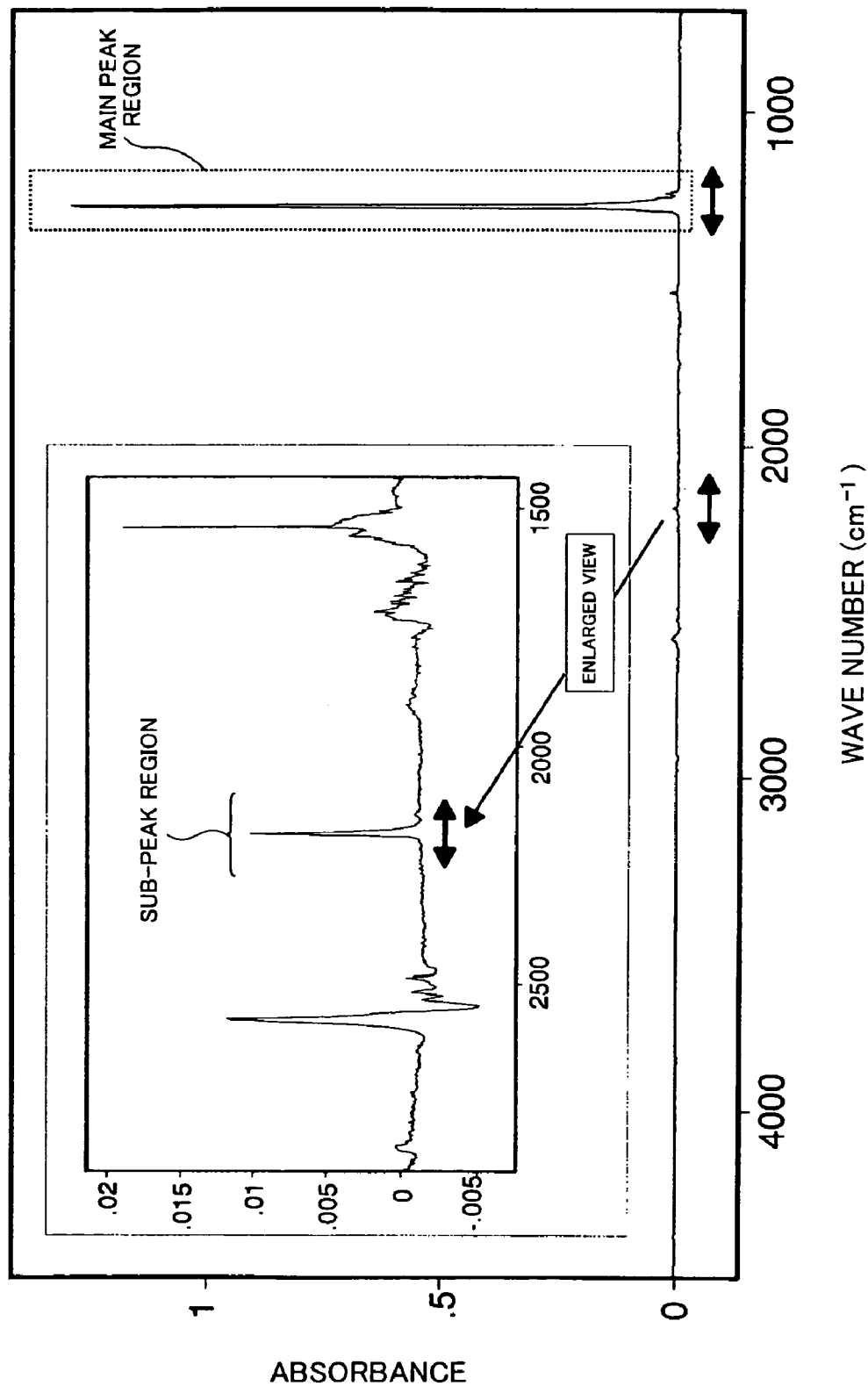
FIG. 8 shows a main peak region and a sub-peak region in a graph showing the relationship between the wave number and absorbance of $CF_4$.
Figure 9A:
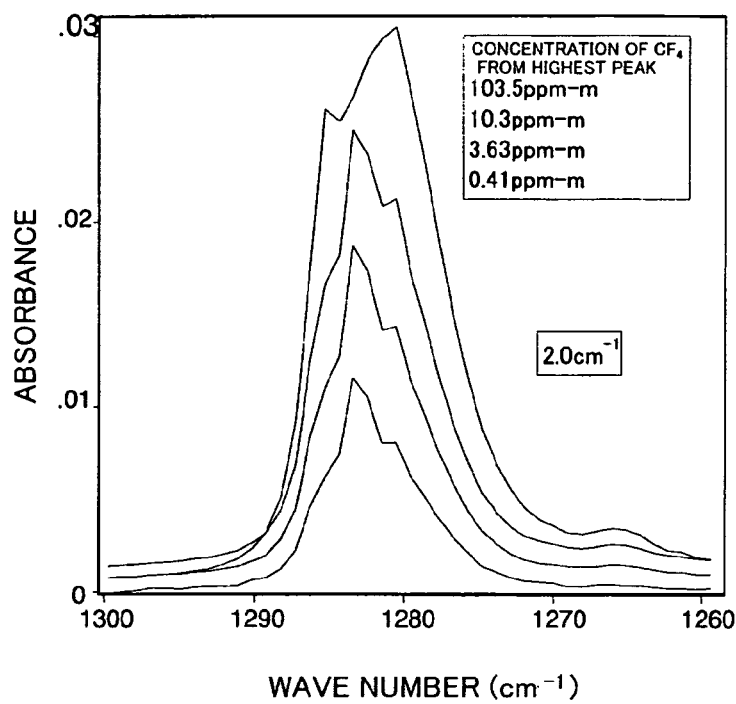
FIGS. 9A and 9B are enlarged views of a main peak region in another graph showing the relationship between the wave number and absorbance of $CF_4$.
Figure 9B:
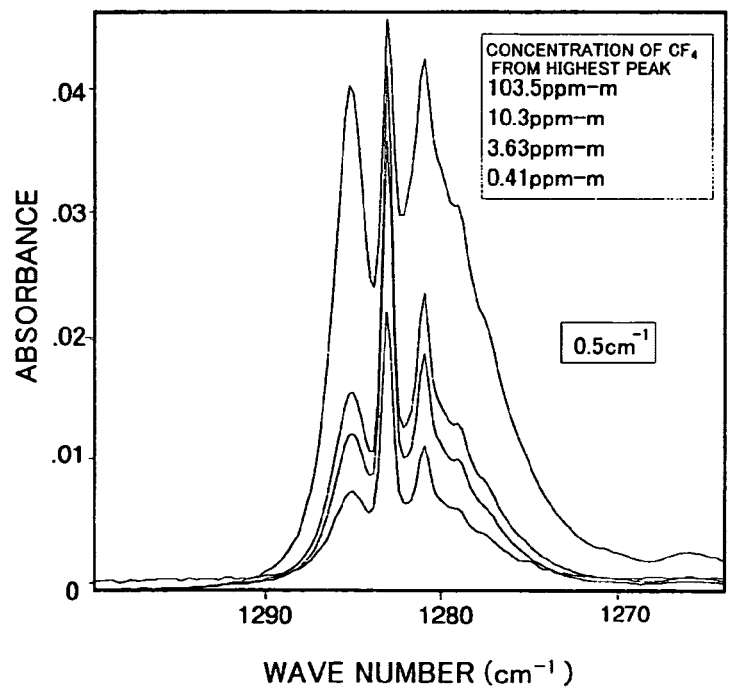

As shown in FIG. 7, $CF_4$ has a main peak region (1230 to 1305 $cm^{-1}$) and a sub-peak region (2160 to 2200 $cm^{-1}$) in the infrared absorption region. FIG. 8 shows the infrared absorption spectrum of $CF_4$ and an enlarged view of the sub-peak region. FIGS. 9A and 9B show enlarged views of the main peak region of $CF_4$. FIG. 9B shows the results measured at a resolving power higher than that of FIG. 9A.

In FIG. 8, the peak which exists in the main peak region of $CF_4$ seems to be a single peak. However, as shown in the enlarged views of FIGS. 9A and 9B, a plurality of peaks exist in the main peak region of $CF_4$. Therefore, in the case of creating the calibration curve based on the main peak region of $CF_4$, an accurate calibration curve is not obtained if the calibration curve is created while ignoring the existence of the peaks shown in FIG. 9B.

FIGS. 9A and 9B show infrared absorption waveforms in the main peak region (1230 to 1305 $cm^{-1}$) in the case where the concentration of $CF_4$ is changed. In more detail, FIGS. 9A and 9B show infrared absorption waveforms in the case where the concentration of $CF_4$ is 103.5 ppm-m, 10.3 ppm-m, 3.63 ppm-m, and 0.41 ppm-m in the order from the highest peak. In FIGS. 9A and 9B, the area (absorption area) enclosed by the waveform and the horizontal axis (wave number) is proportional to the $CF_4$ concentration. Therefore, in the case of calculating the concentration of $CF_4$ included in the sample gas, the absorption area is calculated by referring to FIGS. 9A and 9B after measuring infrared absorption, and the $CF_4$ concentration is calculated from the absorption area by referring to the calibration curve shown in FIG. 7.

In the main peak region of $CF_4$, the height of the peak included in the waveform is increased as the $CF_4$ concentration is increased in the order of 0.41 ppm-m, 3.63 ppm-m, and 10.3 ppm-m, as shown in FIG. 9B. However, even if the $CF_4$ concentration is further increased to 103.5 ppm-m, the height of the highest peak is not increased in proportion to the concentration and is saturated at a certain absorbance. Specifically, in the case of calculating the concentration of $CF_4$ included in the sample gas by using the calibration curve based on the main peak region, the absorption area is not proportional to the $CF_4$ concentration in the region in which the $CF_4$ concentration is high, as shown in FIG. 7. Therefore, an accurate concentration may not be calculated based on the absorption area.

For the reasons described above, reliability of the calibration curve based on the main peak region of $CF_4$ is decreased in the high concentration region. The calibration curve based on the sub-peak region of $CF_4$ may be used in the region in which the $CF_4$ concentration is high. However, the calibration curve based on the sub-peak region excels in linearity in the region in which the $CF_4$ concentration is high, but has poor linearity in the region in which the $CF_4$ concentration is low, as shown in FIG. 7. As shown in FIG. 8, the height of the peak of $CF_4$ which exists in the sub-peak region is very small in comparison with the height of the peak which exists in the main peak region. Therefore, it is difficult to accurately determine the peak of $CF_4$ in the region in which the $CF_4$ concentration is low due to the influence of noise, whereby the amount of error in the $CF_4$ concentration is increased. Therefore, reliability of the resulting $CF_4$ concentration may be decreased if the calibration curve based on the sub-peak region is used in the region in which the $CF_4$ concentration is low.

1-3-2. Effect of Present Embodiment

According to the infrared absorption measurement method in the present embodiment, infrared absorption is measured in a state in which the sample gas including the measurement target component is decompressed, and the absorption area in the peak region of the measurement target component in the infrared absorption shown in a graph which shows the relationship between the wave number and absorbance of the sample gas is calculated. The concentration of the measurement target component in the sample gas is calculated from the absorption area and the pressure of the sample gas during decompression. Specifically, infrared absorption is measured in a state in which the sample gas is decompressed corresponding to the concentration of the measurement target component in the gas to be measured. The absorption area in the peak region of the measurement target component is calculated from the infrared absorption, and the temporary concentration $M_1$ corresponding to the absorption area is calculated by referring to the calibration curve of the measurement target component. If the pressure of the gas including the measurement target component used to create the calibration curve during infrared absorption measurement is $P_1$, and the pressure of the sample gas during decompression is $P_2$, the concentration $M_2$ of the sample gas is calculated by using the above equation (1). Therefore, it is unnecessary to replace the cell corresponding to the concentration of the measurement target component. This reduces cost necessary for measurement. As a result, infrared absorption can be measured at low cost with high accuracy.

According to the infrared absorption measurement method in the present embodiment, the temporary concentration $M_1$ (see equation (1)) can be set within the concentration range which allows the concentration $M_2$ of the measurement target component to be accurately obtained by adjusting the pressure $P_2$ of the sample gas during decompression. This enables the concentration $M_2$ of the measurement target component to be accurately measured based on the equation (1) by utilizing the calibration curve.

In the case where the measurement target component is $CF_4$, since linearity of the calibration curve based on the main peak region is poor in the high concentration region, it is difficult to obtain an accurate concentration in the high concentration region. In this case, if the calibration curve based on the sub-peak region is used, reliability of the calibration curve is decreased due to the influence of noise, whereby an accurate concentration cannot be obtained. On the contrary, according to the infrared absorption measurement method in the present embodiment, the temporary concentration $M_1$ (see equation (1)) can be set within the concentration range which allows accurate measurement to be performed in the calibration curve based on the main peak region by adjusting the pressure $P_2$ of the sample gas during decompression. This enables the concentration $M_2$ of the measurement target component to be accurately measured based on the equation (1) by utilizing the calibration curve based on the main peak region.

Moreover, the period of time necessary for the sample gas to be introduced into the cell 21 and discharged from the cell 21 can be reduced in comparison with the case of measuring the sample gas under normal pressure by measuring the infrared absorption in the cell 21 while introducing the sample gas in a decompressed state. Therefore, the period of time necessary for the measurement can be reduced, whereby efficiency of the measurement can be increased.

The present embodiment illustrates the case where the concentration of $CF_4$ as the measurement target component is calculated by using the calibration curve based on the main peak region. However, whether to use the calibration curve based on either the main peak region or the sub-peak region is judged based on the type of the measurement target component or other components included in the sample gas. This also applies to embodiments described later.

2. Second Embodiment

Figure 2:
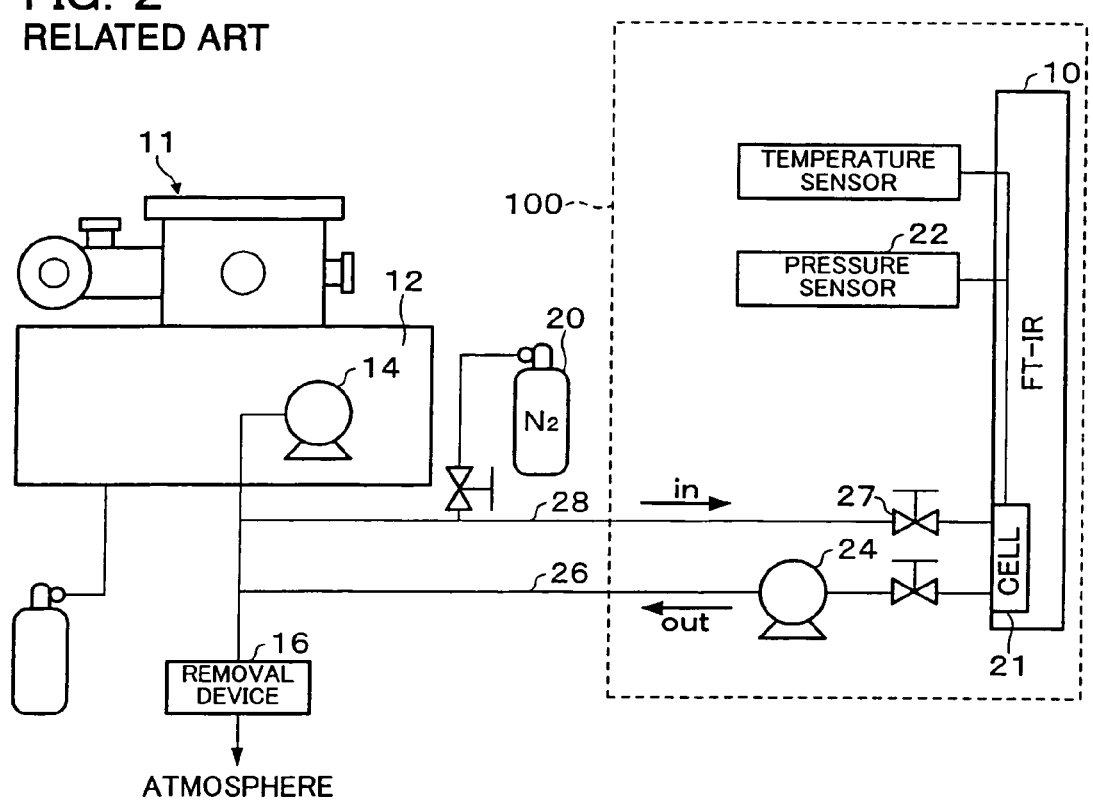
FIG. 2 schematically shows an infrared absorption measurement device in a second embodiment.

FIG. 2 schematically shows semiconductor manufacturing equipment 11 connected with the infrared absorption measurement device 100 in the present embodiment. The present embodiment illustrates the case where the infrared absorption measurement device 100 in the first embodiment is used to quantitatively analyze the measurement target component included in the gas discharged from the semiconductor manufacturing equipment 11.

In the infrared absorption measurement device 100 in the present embodiment, a gas discharged from the semiconductor manufacturing equipment 11 is mixed with nitrogen gas 20 to form a sample gas. The sample gas is introduced into the infrared absorption analysis device 10 through the gas inlet line 28, and infrared absorption of each measurement target component included in the sample gas is measured by using the infrared absorption analysis device 10.

In the semiconductor manufacturing equipment 11, a semiconductor manufacturing process such as dry etching or chemical vapor deposition (CVD) is performed. In the dry etching step, perfluorocarbon (PFC) is used as gas plasma. The present embodiment illustrates the case where $C_4F_8$ (PFC) is used as etching gas. However, the measurement target gas of the infrared absorption measurement device in the present embodiment is not limited to $C_4F_8$.

PFC is one type of greenhouse gas. Greenhouse gases include $CO_2$, $NO_X$, and methane in addition to PFC. These greenhouse gases have a strong absorption in the infrared radiation region, and absorb energy radiated from the earth's surface when released to the atmosphere. The absorbed energy is released to space and the earth's surface. In this case, a part of the energy released from the earth's surface is returned thereto by the greenhouse gases, whereby the temperature of the earth's surface is increased. Greenhouse gases are considered to bring about greenhouse effects through this mechanism.

As an index for comparing the degree of greenhouse effects caused by greenhouse gases, a global warming potential (GWP) has been proposed. GWP indicates the greenhouse effects per unit weight of each gas relative to $CO_2$. PFC is a greenhouse gas having a particularly high greenhouse effect. PFC has an extremely high GWP. For example, the GWP of $CF_4$ is approximately 6500 times that of $CO_2$. PFC is stable in comparison with other gases, and has an extremely long atmospheric lifetime. For example, the atmospheric lifetime of $CF_4$ is approximately 50,000 years. Therefore, PFC warms the earth for many years once it is released to the atmosphere.

PFC is generally used in the manufacturing steps of semiconductor devices, and is widely used in equipment using low pressure plasma. In a dry etching system, PFC such as $CF_4$ or $C_4F_8$ is used to etch $SiO_2$ or $Si_3N_4$. In a CVD system, gas plasma such as $C_2F_6$ is generally used to clean a silicon compound film adhering to the system or the like. A PFC liquid is used as a solvent for cooling a wafer. However, since PFC has a high greenhouse effect as described above, reduction of emission of PFC has been demanded internationally.

In order to demonstrate the reduction of emission of PFC, it is necessary to measure PFC gases emitted from factories. Since it is difficult to actually measure PFC gases emitted from factories, PFC gases emitted from semiconductor manufacturing equipment using PFC is measured, and emission of PFC is determined from the ratio of the gas emitted to the gas used (emission factor) and the amount of gas consumed in factories. The emission factor is calculated by measuring PFC gas actually emitted from the semiconductor manufacturing equipment.

In the case of performing dry etching by using $C_4F_8$ in a chamber 12 of the semiconductor manufacturing equipment 11, $CF_4$, $CHF_3$, $C_2F_4$, $C_2F_6$, $C_3F_8$, $C_4F_8$, $C_5F_8$, $COF_2$, HF, $SiF_4$, $OF_2$, $NF_3$, $SO_2$, $SF_6$, $SO_2F_2$, $SOF_2$, NO, $N_2O$, $NO_2$, CO, and $CO_2$ may be included in the discharged gas depending on the composition of an insulating layer formed on a semiconductor substrate to be processed.

In the case of generating $C_4F_8$ gas plasma in order to perform dry etching in the chamber 12 of the semiconductor manufacturing equipment 11, after evacuating the atmosphere in the chamber 12 by using a pump, a given amount of $C_4F_8$ is introduced into the chamber 12, and a high voltage is applied. This causes $C_4F_8$ gas plasma to be generated. This gas plasma is used for dry etching. In this case, a given percentage of $C_4F_8$ used is decomposed into $CF_4$ and the like, and the remaining $C_4F_8$ is discharged as is from the chamber 12. The discharged gas is absorbed by using a pump 14, and optionally diluted with nitrogen gas supplied from the nitrogen gas cylinder 20 to obtain a sample gas. The sample gas is introduced into the infrared absorption analysis device 10, and infrared absorption of each measurement target component in the sample gas is measured.

The infrared absorption measurement device 100 decompresses the sample gas, as shown in FIG. 1. The sample gas discharged from the semiconductor manufacturing equipment 11 is decompressed by the relationship between the pump 24 and the valve 27, and introduced into the cell 21 of the infrared absorption analysis device 10. Therefore, infrared absorption is measured in the cell 21 in a state in which the sample gas is decompressed. In this case, the pressure of the sample gas may be controlled by the relationship between the pump 24 and the valve 27.

After the measurement, the sample gas is introduced into an removal device 16 from the cell 21 through the discharge line 26. After harmful substances in the sample gas are removed by using the removal device 16, the sample gas is released to the atmosphere.

According to the present embodiment, effects the same as the effects of the infrared absorption measurement method and the measurement apparatus 100 in the first embodiment are obtained. Moreover, according to the present embodiment, each measurement target component in the discharged gas produced in the manufacturing process of semiconductor devices can be analyzed with high accuracy. For example, the concentration of greenhouse gas such as PFC can be accurately measured.

Solid products produced during the manufacturing process are generally included in the gas discharged from the semiconductor manufacturing equipment. In the case where the semiconductor manufacturing process is the etching of an insulating layer, solid products originating from the insulating layer produced by etching are included in the discharged gas. According to the infrared absorption measurement method in the present embodiment, since infrared absorption is measured in the cell 21 in a state in which the sample gas is decompressed, the period of time in which the sample gas resides in the cell 21 is reduced in comparison with the case of measuring the sample gas under normal pressure. This prevents solid products from adhering to the cell 21.

The present embodiment illustrates the case where the infrared absorption measurement device 100 is provided separately from the semiconductor manufacturing equipment 11. However, the infrared absorption measurement device 100 may be provided inside the semiconductor manufacturing equipment 11. This also applies to embodiments described later.

3. Third Embodiment 3-1. Infrared Absorption Measurement Device

Figure 3:
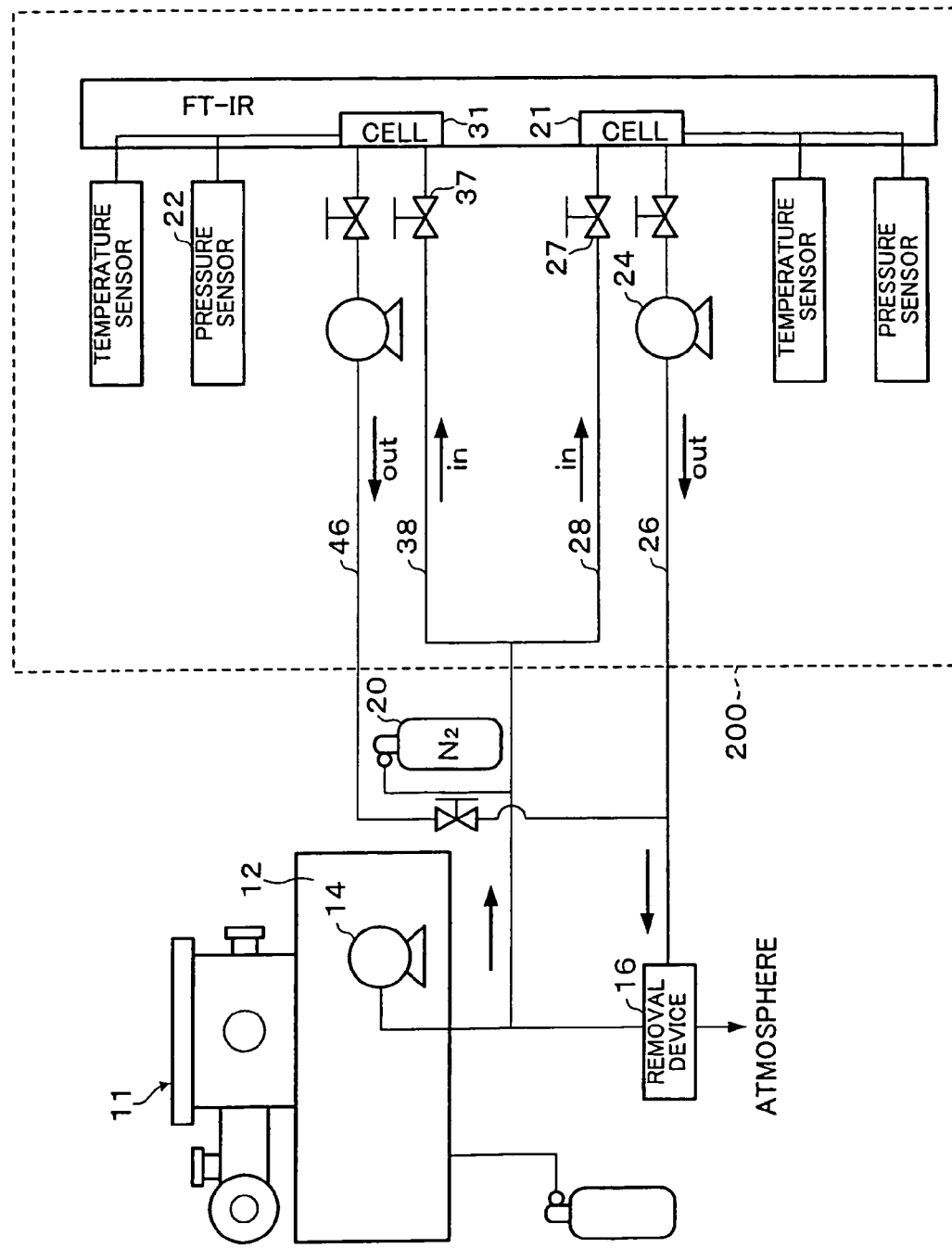
FIG. 3 schematically shows an infrared absorption measurement device in a third embodiment.

FIG. 3 schematically shows an infrared absorption measurement device 200 in the present embodiment and the semiconductor manufacturing equipment 11 connected with the infrared absorption measurement device 200. The present embodiment illustrates the case where the infrared absorption measurement device 200 is used to quantitatively analyze the measurement target component included in the gas discharged from the semiconductor manufacturing equipment 11. Specifically, the present embodiment is the same as the second embodiment in that the infrared absorption measurement device is used to quantitatively analyze the measurement target component included in the gas discharged from the semiconductor manufacturing equipment 11.

The infrared absorption measurement device 200 in the present embodiment has a configuration differing from the configuration of the infrared absorption measurement device 100 in the first embodiment which includes one cell (cell 21) in that the infrared absorption measurement device 200 includes two cells (first and second cells 21 and 31) used for infrared absorption measurement. Elements of the infrared absorption measurement device 200 the same as the elements of the infrared absorption measurement device 100 in the first embodiment are indicated by the same symbols. Detailed description of these elements is omitted here.

In the present embodiment, a gas discharged from the chamber 12 of the semiconductor manufacturing equipment 11 is absorbed by using the pump 14 in the same manner as in the second embodiment. The discharged gas is optionally diluted with nitrogen gas supplied from the nitrogen gas cylinder 20 to obtain a sample gas. The sample gas is introduced into the cells 21 and 31, and infrared absorption of each measurement target component included in the sample gas is measured.

The sample gas including the measurement target component is introduced into the cells 21 and 31 through the gas inlet lines 28 and 38, respectively. The gas inlet lines 28 and 38 respectively introduce the sample gas into the cells 21 and 31. Specifically, after the sample gas is introduced into the cells 21 and 31 through the gas inlet lines 28 and 38, respectively, infrared absorption of each measurement target component included in the sample gas is measured based on the infrared absorption analysis results obtained by using the cells 21 and 31.

As shown in FIG. 3, the infrared absorption measurement device 200 includes the pump 24 and the valve 27 for decompressing the sample gas. The valve 27 is provided in the middle of the gas inlet line (first line) 28. The pump 24 is provided in the middle of the discharge line 26. The sample gas discharged from the semiconductor manufacturing equipment 11 is decompressed by using the pump 24 and the valve 27, and introduced into the cell 21. Therefore, infrared absorption is measured in the cell 21 in a state in which the sample gas is decompressed.

A valve 37 provided in the middle of the gas inlet line (second line) 38 is in an open state in comparison with the valve 27 provided to the gas inlet line 28. Therefore, the sample gas is introduced into the cell 31 under normal pressure. This allows the sample gas to be measured in the cell 31 under normal pressure.

After the measurement, the sample gas is introduced into the removal device 16 from the cells 21 and 31 through the discharge lines 26 and 46, respectively. After harmful substances included in the sample gas are removed by using the removal device 16, the sample gas is released to the atmosphere.

3-2. Infrared Absorption Measurement Method

The infrared absorption measurement method in the present embodiment is described below.

The sample gas is decompressed by the relationship between the pump 24 and the valve 27 before being introduced into the cell 21. Infrared absorption of each measurement target component in the sample gas introduced into the cell 21 is measured by using the same method as in the infrared absorption measurement device 100 in the first embodiment. Specifically, infrared absorption is measured in the cell 21 in a state in which the sample gas is decompressed. The absorption area in the peak region of the measurement target component in the resulting infrared absorption is calculated. The concentration of the measurement target component in the sample gas is calculated from the absorption area and the pressure of the sample gas during decompression. Since the method of calculating the concentration of the measurement target component is described in the first embodiment, detailed description is omitted here.

Infrared absorption of the sample gas introduced into the cell 31 through the gas inlet line 38 is measured under normal pressure. A conventional method is used as a method of calculating the concentration of the measurement target component included in the sample gas based on the resulting infrared absorption. Specifically, the absorption area in the peak region of the measurement target component in the infrared absorption is calculated, and the concentration of the measurement target component included in the sample gas is calculated from the absorption area by using the calibration curve. The calibration curve used herein is a line showing the relationship between the absorption area and the concentration of the measurement target component under normal pressure.

The concentration of the measurement target component obtained by the measurement using the cell 21 is compared with the concentration of the measurement target component obtained by the measurement using the cell 31. If the two concentrations are the same, it is confirmed that the concentrations are accurately measured.

If the concentration of the measurement target component obtained by the measurement using the cell 21 differs from the concentration of the measurement target component obtained by the measurement using the cell 31, one of the concentrations may be used as the measurement result.

As described in the first embodiment (see FIG. 7), in the case where the concentration of $CF_4$ as the measurement target component in the sample gas is low, the amount of noise is relatively larger than the peak which indicates $CF_4$ in the infrared absorption obtained by measuring the sample gas in a decompressed state. Therefore, the resulting $CF_4$ concentration may not be accurate. In this case, the $CF_4$ concentration calculated from the infrared absorption obtained by the measurement using the cell 31, i.e., the $CF_4$ concentration obtained from the infrared absorption of $CF_4$ measured in a state in which the sample gas is under normal pressure may be used as the measurement result.

In the case where the $CF_4$ concentration in the sample gas is high, since linearity of the calibration curve is low in the high concentration region (see FIG. 7), the $CF_4$ concentration calculated from the infrared absorption obtained by measuring the sample gas under normal pressure by using the calibration curve based on the main peak region may not be accurate. In this case, the $CF_4$ concentration calculated from the infrared absorption obtained by the measurement using the cell 21, i.e., the $CF_4$ concentration obtained from the infrared absorption of $CF_4$ measured in a state in which the sample gas is decompressed may be used as the measurement result.

The present embodiment illustrates the case where the sample gas introduced into the cell 21 is decompressed and the sample gas introduced into the cell 31 is under normal pressure. However, the sample gases introduced into the cells 21 and 31 may be decompressed, and the sample gases introduced into the cells 21 and 31 may be under different pressures. In this case, a more accurate $CF_4$ concentration obtained by using the cell 21 or 31 may be used as the measurement result corresponding to the concentration of $CF_4$ included in the sample gas.

3-3. Effect

According to the present embodiment, effects the same as the effects in the first and second embodiments are obtained.

Moreover, according to the present embodiment, since the pressure of the sample gas in the first cell differs from the pressure of the sample gas in the second cell, the concentration of the measurement target component which is measured more accurately can be used as the measurement result.

Specifically, according to the present embodiment, the measurement target components included in the sample gases in the cells 21 and 31 can be measured at the same time in a state in which the sample gas in the cell 21 and the sample gas in the cell 31 are under different pressures, and the concentrations of the measurement target components obtained from the infrared absorption measured by using each of the cells can be compared. Therefore, infrared absorption can be measured with higher accuracy.

4. Fourth Embodiment 4-1. Infrared Absorption Measurement Device

Figure 4:
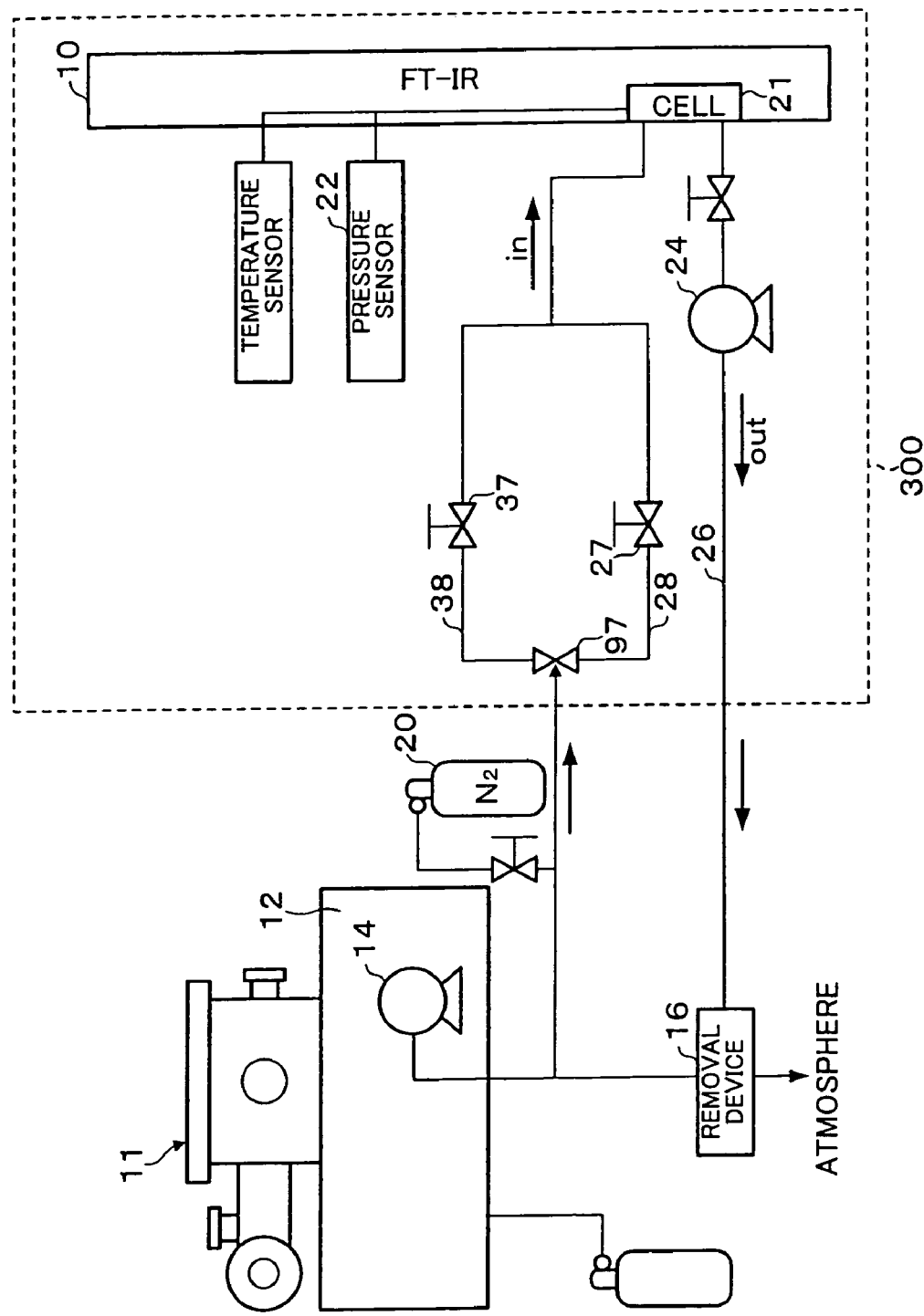
FIG. 4 schematically shows an infrared absorption measurement device in a fourth embodiment.

FIG. 4 schematically shows an infrared absorption measurement device 300 in the present embodiment and the semiconductor manufacturing equipment 11 connected with the infrared absorption measurement device 300. The present embodiment illustrates the case where the infrared absorption measurement device 300 is used to quantitatively analyze the measurement target component included in the gas discharged from the semiconductor manufacturing equipment 11. Specifically, the present embodiment is the same as the second embodiment in that the infrared absorption measurement device is used to quantitatively analyze the measurement target component included in the gas discharged from the semiconductor manufacturing equipment 11.

The infrared absorption measurement device 300 in the present embodiment has a configuration differing from the configuration of the infrared absorption measurement device 100 in the second embodiment in that the infrared absorption measurement device 300 includes a three-way valve (gas inlet switch section) 97, and the gas inlet lines 28 and 38 are connected in parallel with the three-way valve 97. Elements of the infrared absorption measurement device 300 the same as the elements of the infrared absorption measurement device 100 in the second embodiment are indicated by the same symbols. Detailed description of these elements is omitted here.

In the present embodiment, a gas discharged from the chamber 12 of the semiconductor manufacturing equipment 11 is absorbed by using the pump 14 in the same manner as in the second and third embodiments. The discharged gas is optionally diluted with nitrogen gas supplied from the nitrogen gas cylinder 20 to obtain a sample gas. The sample gas is introduced into the cell 21, and infrared absorption of each measurement target component in the sample gas is measured.

The sample gas including the measurement target component is introduced into the cell 21 through either the gas inlet line (first line) 28 or the gas inlet line (second line) 38. Specifically, the sample gas is introduced into the cell 21 through either the gas inlet line 28 or the gas inlet 38, and infrared absorption of each measurement target component in the gas is measured based on the infrared absorption analysis results obtained by using the cell 21.

The gas inlet lines 28 and 38 are connected in parallel with the three-way valve 97. The sample gas is introduced into the cell 21 through either the gas inlet line 28 or the gas inlet line 38 by switching the direction of the plug of the three-way valve 97. Specifically, the three-way valve 97 has a function of introducing the sample gas into either the gas inlet line 28 or the gas inlet line 38.

As shown in FIG. 4, the valve 27 for decompressing the sample gas is provided to the gas inlet line 28. The valve 27 is provided in the middle of the gas inlet line 28. In the infrared absorption measurement device 300, the pump 24 is provided in the middle of the discharge line 26. Therefore, in the case where the sample gas is introduced into the cell 21 through the gas inlet line 28, the sample gas is decompressed by using the pump 24 and the valve 27 and introduced into the cell 21. In this case, infrared absorption is measured in the cell 21 in a state in which the sample gas is decompressed.

The valve 37 provided in the middle of the gas inlet line 38 is in an open state differing from the gas inlet line 28. Therefore, in the case where the sample gas is introduced into the cell 21 through the gas inlet line 38, the sample gas is introduced into the cell 21 under normal pressure. In this case, the sample gas is measured in the cell 21 under normal pressure.

After the measurement, the sample gas is introduced into the removal device 16 from the cell 21 through the discharge line 26. After harmful substances in the sample gas are removed by using the removal device 16, the sample gas is released to the atmosphere.

The present embodiment illustrates the case where the sample gas introduced through the gas inlet line 28 is in a decompressed state and the sample gas introduced through the gas inlet line 38 is under normal pressure. However, in the infrared absorption measurement device 300 in the present embodiment, the sample gases introduced through the gas inlet lines 28 and 38 may be decompressed, and the sample gases introduced through the gas inlet lines 28 and 38 may be under different pressures.

In the infrared absorption measurement device 300 in the present embodiment, the valve 37 formed of a needle valve may be provided to the gas inlet line 38, for example. The pressure of the sample gas may be controlled by using the valve 37. In this case, the sample gas may be introduced into the cell 21 through either the gas inlet line 28 or the gas inlet line 38 by switching the plug of the three-way valve 97 corresponding to the concentration of $CF_4$ included in the sample gas. Specifically, the sample gas may be introduced into the cell 21 while selecting either the gas inlet line 28 or the gas inlet line 38 corresponding to the concentration of $CF_4$ included in the sample gas. Therefore, the sample gas in the cell 21 can be set under a more suitable pressure in infrared absorption measurement corresponding to the concentration of the measurement target component ($CF_4$) in the sample gas. This enables the $CF_4$ concentration obtained from the infrared absorption to be set within a suitable concentration range. As a result, a more accurate $CF_4$ concentration can be used as the measurement result.

4-2. Infrared Absorption Measurement Method

The infrared absorption measurement method in the present embodiment is described below.

The sample gas is introduced through the gas inlet line 28 by switching the plug of the three-way valve 97. In this case, the sample gas is decompressed by using the pump 24 and the valve 27, and introduced into the cell 21. Infrared absorption of each measurement target component in the sample gas introduced into the cell 21 is measured by using the same method as in the infrared absorption measurement device 100 in the first embodiment. Specifically, the infrared absorption is measured in the cell 21 in a state in which the sample gas is decompressed, and the absorption area in the peak region of the measurement target component in the infrared absorption is calculated. The concentration of the measurement target component in the sample gas is calculated from the absorption area and the pressure of the sample gas during decompression. Since the method of calculating the concentration of the measurement target component is described in the first embodiment, detailed description is omitted here.

The sample gas is introduced through the gas inlet line 38 by switching the plug of the three-way valve 97. In this case, infrared absorption of the sample gas introduced into the cell 21 through the gas inlet line 38 is measured under normal pressure. A conventional method is used as a method of calculating the concentration of the measurement target component in the sample gas based on the resulting infrared absorption. Specifically, the absorption area in the peak region of the measurement target component in the resulting infrared absorption is calculated, and the concentration of the measurement target component in the sample gas is calculated from the absorption area by using the calibration curve. The calibration curve used herein is a line showing the relationship between the absorption area and the concentration of the measurement target component under normal pressure.

As described in the first embodiment (see FIG. 7), in the case where the concentration of $CF_4$ as the measurement target component in the sample gas is low, the amount of noise is relatively larger than the peak which indicates $CF_4$ in the infrared absorption obtained by measuring the sample gas in a decompressed state. Therefore, the resulting $CF_4$ concentration may not be accurate. In this case, the sample gas is introduced into the cell 21 through the gas inlet line 38 by switching the three-way valve 97. In this case, the $CF_4$ concentration obtained from the infrared absorption of $CF_4$ measured in a state in which the sample gas is under normal pressure may be used as the measurement result.

In the case where the $CF_4$ concentration in the sample gas is high, since linearity of the calibration curve is poor in the high concentration region (see FIG. 7), the $CF_4$ concentration calculated from the infrared absorption obtained by measuring the sample gas under normal pressure by using the calibration curve based on the main peak region may not be accurate. In this case, the sample gas is introduced into the cell 21 through the gas inlet line 28 by switching the three-way valve 97. Therefore, the $CF_4$ concentration obtained from the infrared absorption of $CF_4$ measured in a state in which the sample gas is decompressed may be used as the measurement result.

4-3. Effect

According to the present embodiment, effects the same as the effects in the first and second embodiments are obtained.

Moreover, according to the present embodiment, since the pressure of the sample gas introduced through the gas inlet line 28 differs from the pressure of the sample gas introduced through gas inlet line 38, the sample gas can be measured under a more suitable pressure corresponding to the concentration of the measurement target component. This enables the concentration of the measurement target component to be measured more accurately.

Furthermore, infrared absorption can be measured by introducing the decompressed sample gas through the gas inlet line 28 when the concentration of the measurement target component is high, and introducing the sample gas under normal pressure through the gas inlet line 38 when the concentration of the measurement target component is low, by switching the three-way valve 97. This makes it unnecessary to replace the cell corresponding to the concentration of the measurement target component included in the sample gas. Therefore, cost can be reduced.

5. Fifth Embodiment 5-1. Infrared Absorption Measurement Device

Figure 5:
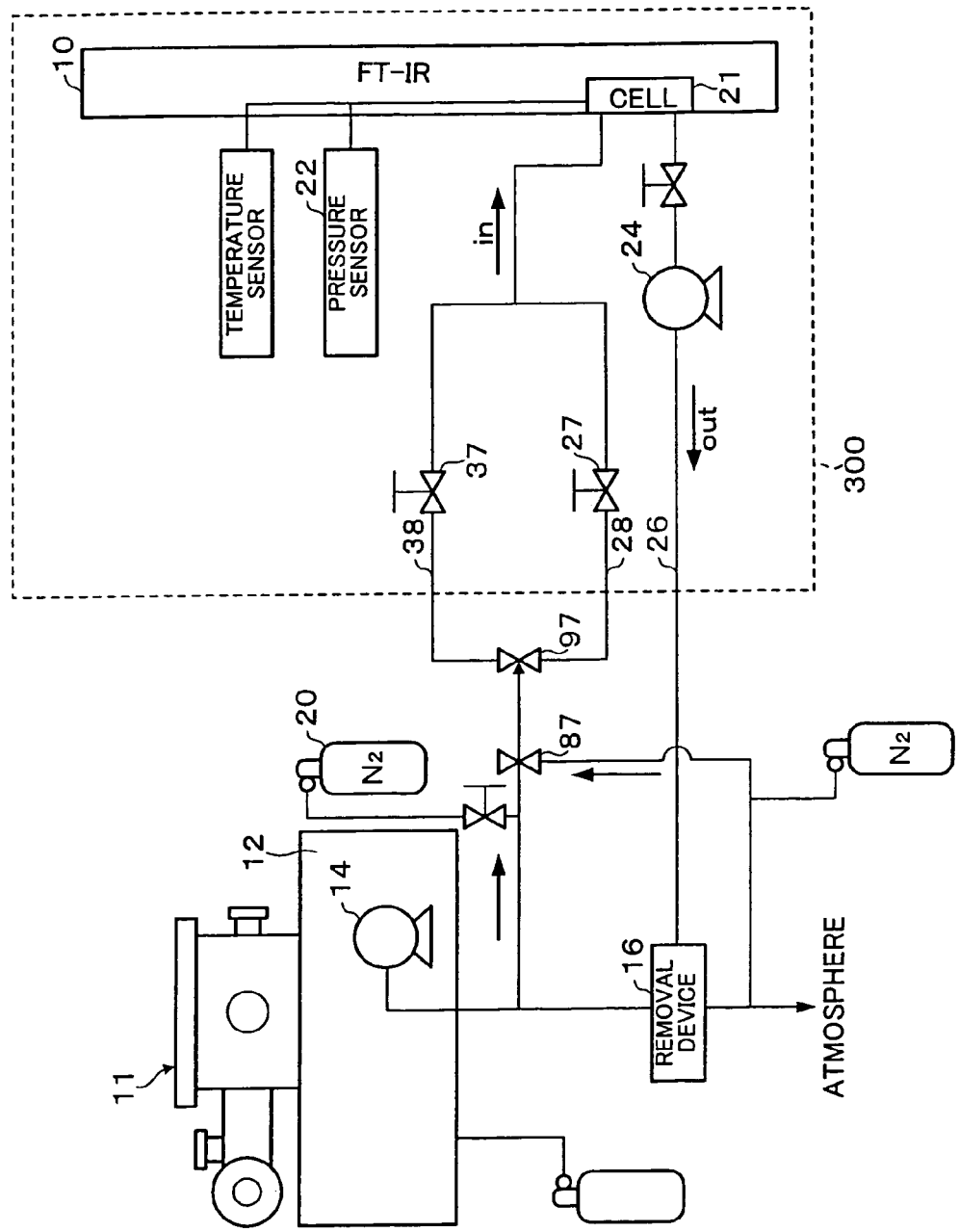
FIG. 5 schematically shows an infrared absorption measurement device in a fifth embodiment.

FIG. 5 schematically shows the infrared absorption measurement device 300 in the present embodiment and the semiconductor manufacturing equipment 11 connected with the infrared absorption measurement device 300. The present embodiment illustrates the case where the infrared absorption measurement device 300 is used to quantitatively analyze the measurement target component in the gas discharged from the semiconductor manufacturing equipment 11 in the same manner as in the fourth embodiment.

The infrared absorption measurement device 300 in the present embodiment has a configuration differing from the configuration in the fourth embodiment in that the infrared absorption measurement device 300 is installed to measure the concentration of the discharged gas before and after passing through the removal device 16 connected with the semiconductor manufacturing equipment 11.

In the present embodiment, a gas discharged from the chamber 12 of the semiconductor manufacturing equipment 11 is absorbed by using the pump 14 in the same manner as in the second to fourth embodiments. The discharged gas is optionally diluted with nitrogen gas supplied from the nitrogen gas cylinder 20 to obtain a sample gas. The sample gas is introduced into the cell 21, and infrared absorption of each measurement target component in the sample gas is measured.

The sample gas is introduced into the removal device 16 from the cell 21 through the discharge line 26. After harmful substances in the sample gas are removed by using the removal device 16, the sample gas is released to the atmosphere. In the present embodiment, the gas discharged from the removal device 16 is also introduced into the cell 21, and infrared absorption of each measurement target component in the sample gas is measured.

5-2. Infrared Absorption Measurement Method

The infrared absorption measurement method in the present embodiment is described below.

The case of measuring the measurement target component in the gas discharged from the chamber 12 of the semiconductor manufacturing equipment 11 is described below. The discharged gas is diluted with the nitrogen gas 20 to obtain a sample gas as described above. Since the discharged gas has not passed through the removal device 16, the concentration of the measurement target component is higher than that of the gas discharged through the removal device 16.

The sample gas including the gas discharged from the chamber 12 of the semiconductor manufacturing equipment 11 is introduced into the three-way valve 97 by adjusting a three-way valve 87. The sample gas is then introduced into the gas inlet line 28 by adjusting the three-way valve 97. The sample gas may be decompressed by closing the valve 27. In the infrared absorption measurement device 300, the pressure of the sample gas may be adjusted by switching the three-way valve 97 and the difference in the degree of closing of the valve 27 and the valve 37. In this case, the sample gas is decompressed before being introduced into the cell 21. Infrared absorption of each measurement target component in the sample gas introduced into the cell 21 is measured by using the same method as in the infrared absorption measurement device 100 in the first embodiment. Specifically, infrared absorption is measured in the cell 21 in a state in which the sample gas is decompressed, and the absorption area in the peak region of the measurement target component in the infrared absorption is calculated. The concentration of the measurement target component in the sample gas is calculated from the absorption area and the pressure of the sample gas during decompression. Since the method of calculating the concentration of the measurement target component is described in the first embodiment, detailed description is omitted here.

The case of measuring the measurement target component in the gas discharged from the removal device 16 is described below. In this case, whether or not the removal device 16 operates normally can be confirmed by confirming whether or not the measurement target component remains in the discharged gas. Since the discharged gas has passed through the removal device 16, the concentration of the measurement target component is lower than that of the discharged gas before passing through the removal device 16.

The sample gas including the gas discharged from the removal device 16 is introduced into the three-way valve 97 by adjusting the three-way valve 87. The sample gas is introduced into the gas inlet line 38 by adjusting the three-way valve 97. The sample gas may be set to a state closer to normal pressure by opening the valve 37. Infrared absorption of the sample gas introduced into the cell 21 through the gas inlet line 38 is measured under normal pressure. A conventional method is used as a method of calculating the concentration of the measurement target component in the sample gas based on the resulting infrared absorption. Specifically, the absorption area in the peak region of the measurement target component in the resulting infrared absorption is calculated, and the concentration of the measurement target component in the sample gas is calculated from the absorption area by using the calibration curve. The calibration curve used herein is a line showing the relationship between the absorption area and the concentration of the measurement target component under normal pressure.

The description is given taking the case of using $CF_4$ as the measurement target component as an example, as described in the first embodiment (see FIG. 7). The $CF_4$ concentration in the gas after passing through the removal device 16 (discharged gas) is lower than that in the discharged gas before passing through the removal device 16. In the case where the $CF_4$ concentration in the sample gas is low, the amount of noise is relatively larger than the peak which indicates $CF_4$ in the infrared absorption obtained by measuring the sample gas in a decompressed state. Therefore, the resulting $CF_4$ concentration may not be accurate. In this case, the sample gas is introduced into the cell 21 through the gas inlet line 38 by switching the three-way valve 97. Therefore, the $CF_4$ concentration obtained from the infrared absorption of $CF_4$ measured in a state in which the sample gas is under normal pressure may be employed as the $CF_4$ concentration in the discharged gas after passing through the removal device 16.

The $CF_4$ concentration in the discharged gas before passing through the removal device 16 is higher than that of the gas after passing through the removal device 16 (discharged gas). In the case where the $CF_4$ concentration in the sample gas is high, since linearity of the calibration curve based on the main peak region is poor in the high concentration region (see FIG. 7), the $CF_4$ concentration calculated from the infrared absorption obtained by measuring the sample gas under normal pressure by using the calibration curve may not be accurate. In this case, the sample gas is introduced into the cell 21 through the gas inlet line 28 by switching the three-way valve 97. Therefore, the $CF_4$ concentration obtained from the infrared absorption of $CF_4$ measured in a state in which the sample gas is decompressed may be employed as the $CF_4$ concentration in the discharged gas before passing through the removal device 16.

If the $CF_4$ concentration in the discharged gas before passing through the removal device 16 is $C_1$, and the $CF_4$ concentration in the discharged gas after passing through the removal device 16 is $C_2$, the $CF_4$ removal percentage X (%) of the removal device is expressed by the following equation (2).

$$X = (1 - C_2/C_1) \times 100 \qquad (2)$$

As described above, according to the present embodiment, the removal percentage X of a specific component ($CF_4$ in this example) in the removal device 16 can be calculated. As a result, the removal performance of the removal device 16 can be evaluated.

5-3. Effect

According to the present embodiment, effects the same as the effects in the fourth embodiment are obtained.

Moreover, a more accurate concentration of the measurement target component in the gas before and after passing through the removal device 16 can be obtained. Specifically, since the infrared absorption of the measurement target component can be measured by changing the pressure of the sample gas corresponding to the concentration of the measurement target component, the concentration of the measurement target component in the gas before and after passing through the removal device 16 can be obtained by using the calibration curve based on the same peak region. This enables the concentration of the measurement target component to be obtained more accurately.

The present invention is not limited to the above-described embodiments. Various modifications and variations are possible. For example, the present invention includes configurations essentially the same as the configurations described in the embodiments (for example, configurations having the same function, method, and results, or configurations having the same object and results). The present invention includes configurations in which any unessential part of the configuration described in the embodiments is replaced. The present invention includes configurations having the same effects or achieving the same object as the configurations described in the embodiments. The present invention includes configurations in which conventional technology is added to the configurations described in the embodiments.

6. Experiment Example

An experiment example of the present invention is described below. This experiment example shows results for infrared absorption measurement on the sample gas including $SF_6$ as the measurement target component by using the infrared absorption measurement device 100 shown in FIG. 1. In more detail, the sample gas obtained by mixing $SF_6$ with nitrogen gas was introduced into the cell at a known flow rate. The sample gas was decompressed by using the pump, and introduced into the cell to measure infrared absorption. The flow rate of $SF_6$ was 12.5, 25, 50, and 100 (cc/min). The flow rate of $SF_6$ is generally proportional to the concentration of $SF_6$. In this experiment example, a cell having a length of 1 cm was used for infrared absorption measurement. The absorption area of $SF_6$ in the main peak region (910 to 1009 $cm^{-1}$) was measured, and the quantity of $SF_6$ was determined by using the calibration curve based on the main peak region. The calibration curve used in this experiment example was created based on data (concentration and absorption area of $SF_6$) measured under atmospheric pressure.

Infrared absorption of the sample gas at each concentration was measured, and the absorption area of $SF_6$ was calculated from the resulting infrared absorption waveform. The temporary concentration of $SF_6$ was calculated from the absorption area by referring to the calibration curve. If the temporary concentration is $M_1$, the pressure of the gas including the measurement target component used to create the calibration curve during infrared absorption measurement is $P_1$, and the pressure of the sample gas during decompression is $P_2$, the concentration $M_2$ of $SF_6$ in the sample gas is expressed by the above equation (1). The concentration $M_2$ of $SF_6$ in the sample gas at each concentration was calculated by using the equation (1).

Figure 10:
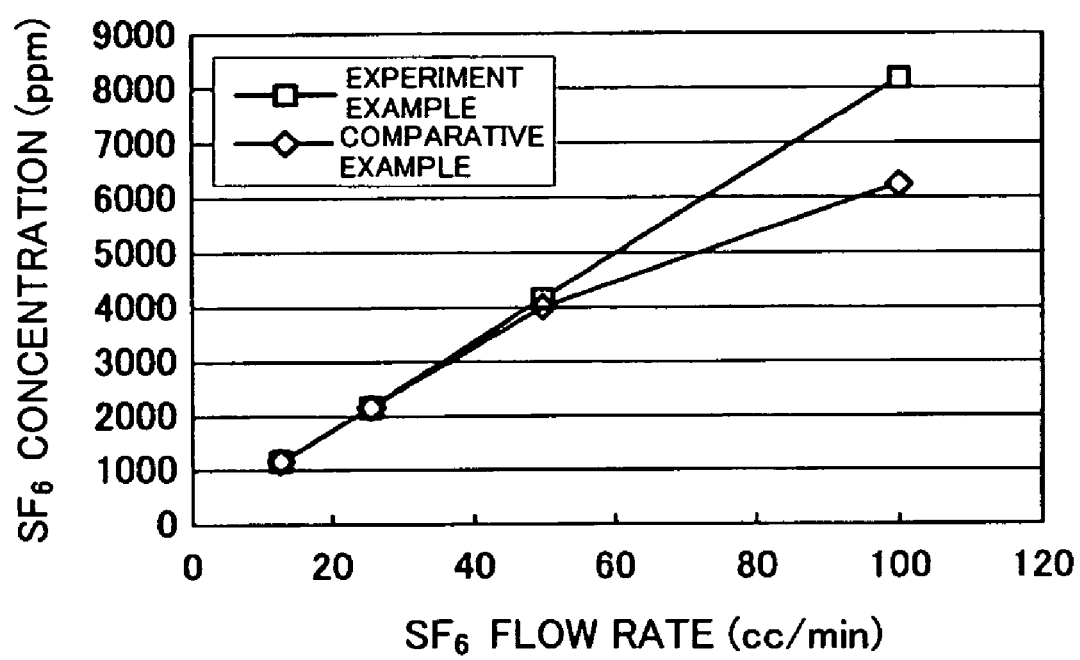
FIG. 10 shows the relationship between concentration and flow rate of a measurement target component ($SF_6$) in infrared absorption measurement in an experiment example of the present invention.

The relationship between the flow rate of $SF_6$ and the concentration ($M_2$) of $SF_6$ of the sample gas at each concentration is shown in FIG. 10. FIG. 10 also shows results for infrared absorption of the sample gas at each concentration measured without decompressing the sample gas as a comparative example.

In the experiment example, in the case where the sample gas including $SF_6$ was introduced into the cell under reduced pressure at each of the above flow rates, the calculated $SF_6$ concentration was proportional to the flow rate, as shown in FIG. 10.

In the case of using $SF_6$ as the sample gas, since linearity of the calibration curve is generally poor in the high concentration region in the same manner as in the case of using $CF_4$ as described in the first embodiment, an accurate concentration may not be obtained. As shown in FIG. 10, in the comparative example, the proportional relationship was established between the flow rate of $SF_6$ and the $SF_6$ concentration in the region in which the $SF_6$ concentration was low. However, the proportional relationship was not established between the flow rate of $SF_6$ and the $SF_6$ concentration in the comparative example in the region in which the $SF_6$ concentration was high (flow rate of $SF_6$ was 100 (cc/min) in more detail). Specifically, an increase in the $SF_6$ concentration was reduced in the comparative example as the flow rate of $SF_6$ was increased in the region in which the flow rate of $SF_6$ was high.

In the experiment example, the proportional relationship was established between the flow rate of $SF_6$ and the $SF_6$ concentration by decompressing the sample gas including $SF_6$, even in the region in which the flow rate of $SF_6$ was high.

As described above, according to this experiment example, the $SF_6$ concentration could be measured with high accuracy by decompressing the sample gas including $SF_6$.

What is claimed is:

1. An infrared absorption measurement method comprising:
   (a) measuring infrared absorption of a measurement target component in a state in which a sample gas including the measurement target component is decompressed;
   (b) calculating an absorption area in a peak region of the measurement target component in the infrared absorption shown in a graph which shows the relationship between the wave number and absorbance of the sample gas;
   (c) calculating a concentration of the measurement target component in the sample gas based on the absorption area and pressure of the sample gas during decompression;
   (d) measuring the infrared absorption of the measurement target component in the sample gas under pressure differing from the pressure of the sample gas in the step (a);
   (e) calculating the absorption area based on the peak region of the measurement target component in the infrared absorption measured in the step (d);
   (f) calculating the concentration of the measurement target component in the sample gas based on the absorption area calculated in the step (e) and the pressure of the sample gas in the step (d); and
   (g) comparing the concentration of the measurement target component calculated in the step (c) with the concentration of the measurement target component calculated in the step (f).

2. The infrared absorption measurement method as defined in claim 1,
   wherein a temporary concentration $M_1$ corresponding to the absorption area is calculated in the step (c) by referring to a calibration curve which represents a relationship between the concentration and absorption area of a reference gas including the target component, and
   wherein, when pressure of the reference gas including the measurement target component used to create the calibration curve during infrared absorption measurement is $P_1$ and the pressure of the sample gas during the decompression is $P_2$, a concentration $M_2$ of the sample gas is expressed by the following equation.

$$M_2 = M_1 P_1 / P_2$$

3. The infrared absorption measurement method as defined in claim 1,
   wherein an infrared absorption region of the measurement target component shown in the graph includes a main peak region and a sub-peak region in an infrared absorption region, and
   wherein the peak region is the main peak region.

4. The infrared absorption measurement method as defined claim 1, wherein the pressure of the sample gas in the step (d) is normal pressure.

5. The infrared absorption measurement method as defined in claim 1, wherein the measurement target component is included in a gas discharged from semiconductor manufacturing equipment.

6. A method of manufacturing a semiconductor device, comprising:

calculating a concentration of a measurement target component in a sample gas by using the infrared absorption measurement method as defined in claim 1, wherein the measurement target component is included in a gas discharged from semiconductor manufacturing equipment.

7. An infrared absorption measurement device comprising:

a pump which decompresses a sample gas including a measurement target component; and an infrared absorption analysis device with a first cell and a second cell containing the sample gas at two different pressures, the infrared absorption analysis device measures infrared absorption of the measurement target component in the sample gas decompressed by the pump.

8. An infrared absorption measurement device comprising:

an infrared absorption analysis device which includes first and second cells for measuring infrared absorption and measures infrared absorption of a measurement target component in a sample gas;

a first line for introducing the sample gas into the first cell; and a second line for introducing the sample gas into the second cell, wherein pressure of the sample gas in the first cell differs from pressure of the sample gas in the second cell.

9. The infrared absorption measurement device as defined in claim 8, wherein the infrared absorption of the measurement target component in the sample gas in the first cell and the infrared absorption of the measurement target component in the sample gas in the second cell are measured at the same time.

10. An infrared absorption measurement device comprising:

an infrared absorption analysis device which includes a cell for measuring infrared absorption and measures infrared absorption of a measurement target component in a sample gas;

a sample gas inlet switch section; and first and second lines which are connected in parallel with the sample gas inlet switch section and introduce the sample gas into the cell, wherein the sample gas inlet switch section has a function of introducing the sample gas into one of the first line and the second line, wherein the sample gas is introduced into the cell from one of the first line and the second line, and wherein pressure of the sample gas introduced into the cell from the first line differs from pressure of the sample gas introduced into the cell from the second line.

11. The infrared absorption measurement device as defined in claim 10, wherein the sample gas inlet switch section is a three-way valve, and wherein the sample gas is introduced into the cell from one of the first line and the second line by switching the three-way valve.

* * * * *